(12) United States Patent
Delalleau et al.

(10) Patent No.: US 7,960,438 B2
(45) Date of Patent: *Jun. 14, 2011

(54) USE OF AGOMELATINE IN OBTAINING MEDICAMENTS INTENDED FOR THE TREATMENT OF GENERALIZED ANXIETY DISORDER

(75) Inventors: Bruno Delalleau, Asnieres-sur-Seine (FR); Agnes Fabiano, Ville d'Avray (FR); Mark Millan, Le Pecq (FR); Elisabeth Mocaer, Neuilly sur Seine (FR)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/732,762

(22) Filed: Apr. 4, 2007

(65) Prior Publication Data

US 2007/0238792 A1 Oct. 11, 2007

Related U.S. Application Data

(60) Provisional application No. 60/790,359, filed on Apr. 7, 2006.

(30) Foreign Application Priority Data

Apr. 7, 2006 (FR) ..................... 06 03083

(51) Int. Cl.
*A61K 31/07* (2006.01)
(52) U.S. Cl. ....................................... 514/740
(58) Field of Classification Search ............. 514/630, 514/740
See application file for complete search history.

(56) References Cited

U.S. PATENT DOCUMENTS

| 5,194,614 | A  | * | 3/1993 | Andrieux et al. | 544/400 |
| 5,225,442 | A  | * | 7/1993 | Andrieux et al. | 514/613 |
| 5,318,994 | A  | * | 6/1994 | Andrieux et al. | 514/613 |
| 7,250,531 | B2 | * | 7/2007 | Souvie et al. | 564/172 |
| 7,358,395 | B2 | * | 4/2008 | Coquerel et al. | 564/172 |
| 2005/0164987 | A1 | * | 7/2005 | Barberich | 514/58 |
| 2006/0205754 | A1 | * | 9/2006 | Willigers | 514/288 |
| 2006/0270876 | A1 | * | 11/2006 | Coquerel et al. | 564/219 |
| 2007/0185080 | A1 | * | 8/2007 | Eriksson et al. | 514/211.13 |

FOREIGN PATENT DOCUMENTS

| EP | 0447285 | 9/1991 |
| EP | 1564202 | 8/2005 |
| WO | 2005/002562 | 1/2005 |
| WO | 2006/096434 | 9/2006 |

OTHER PUBLICATIONS

Servier Labortories (FR) Agomelatine S-20098, Drugs of the Future 2003, 28(1): 7-13.*
E. Mocaer, et al., "Development of 1-4 a new antidepressant: agomelatine" Medecine Sciences, vol. 21, No. 10, Oct. 2005.
S.A. Montgomery, et al., "Absence of discontinuation symptoms with agomelatine and occurrence of discountinuation symptoms with paroxetine: a randomized double-blind, placebo-controlled discontinuation study" International Clinical Psychopharmacology, vol. 19, No. 5, Sep. 2004.
French Preliminary Search Report for FR06/03083 of Nov. 21, 2006.
Diagnostic Criteria for Generalized Anxiety Disorder, *Diagnostic and Statistical Manual of Mental Disorders*, Fourth Edition, Text Revision, 2000.

* cited by examiner

*Primary Examiner* — Jennifer M Kim
(74) *Attorney, Agent, or Firm* — Hueschen and Sage

(57) ABSTRACT

The present invention relates to the use of agomelatine, or N-[2-(7-methoxy-1-naphthyl)ethyl]acetamide, in obtaining medicaments intended for the treatment of Generalized Anxiety Disorder.

5 Claims, No Drawings

USE OF AGOMELATINE IN OBTAINING MEDICAMENTS INTENDED FOR THE TREATMENT OF GENERALIZED ANXIETY DISORDER

The present invention relates to the use of agomelatine, or N-[2-(7-methoxy-1-naphthyl)ethyl]acetamide of formula (I):

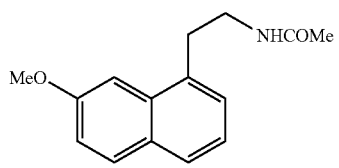

and also its hydrates, crystalline forms and addition salts with a pharmaceutically acceptable acid or base, in obtaining medicaments intended for the treatment of Generalized Anxiety Disorder or GAD.

Agomelatine, or N-[2-(7-methoxy-1-naphthyl)ethyl]acetamide, has the double characteristic of being, on the one hand, an agonist of receptors of the melatoninergic system and, on the other hand, an antagonist of the 5-HT$_{2C}$ receptor. These properties provide it with activity in the central nervous system and, more especially, in the treatment of major depression, seasonal affective disorder, sleep disorders, cardiovascular pathologies, pathologies of the digestive system, insomnia and fatigue due to jet-lag, appetite disorders and obesity.

Agomelatine, its preparation and its use in therapeutics have been described in European Patent Specifications EP 0 447 285 and EP 1 564 202.

The Applicant has now found that agomelatine, or N-[2-(7-methoxy-1-naphthyl)ethyl]-acetamide, and also its hydrates, crystalline forms and addition salts with a pharmaceutically acceptable acid or base, has valuable properties allowing their use in the treatment of Generalized Anxiety Disorder.

Characterized by a considerable and unfounded anxiety, Generalized Anxiety Disorder meets very well defined criteria and constitute a full nosographic entity (300.02—DSM IV—Mental Troubles Diagnostic and Statistic handbook, 4$^{th}$ edition, American Psychiatric Association). This chronic pathology leads to numerous associated troubles, and especially cognitive dysfunctions, more particularly concerning thought and mental representations, changes in reasoning, in judgment and therefore in performances, but it also leads to psychomotor troubles source of awkwardness, weakened capacity to react or even no capacity to react (Wittchen H U et al., Arch Gen Psychiatry, 1994, 51(5), 355-364).

The specificity for that condition is elsewhere recognized by the American and European health authorities who have published guidelines for the development of drugs specifically claiming this indication (Committee for Proprietary Medicinal Products (CPMP)/EWP/4284/02/London—20 Jan. 2005—Guideline on the clinical investigation for the treatment of medicinal products indicated for Generalized Anxiety Disorder).

Recent epidemiological studies show a prevalence of 5 to 6% of the world population for this pathology and up to 10% in women more than 40 years old. The impact for this pathological condition from both health and economic points of view is therefore important.

There is currently no fully satisfactory, recognised treatment for the Generalized Anxiety Disorder. Benzodiazepines were first-line treatments for a long time, and are still used in some countries.

More recently, administration of molecules such as venlafaxine, paroxetine or escitalopram have been recommended. Nevertheless numerous side effects have been listed for those different treatments, the most frequently reported ones being sedation, pharmaco-dependency, alcohol interaction, and a non negligible impact on cardiovascular and/or sexual aspects. Elsewhere, in most cases, stopping of the treatments leads to a discontinuation syndrome, which is not acceptable for patients.

Thus, as underlined in the guideline CPMP, the elaboration of new treatments for this pathology is a necessity.

Agomelatine, new chemical entity with innovative pharmacological properties, showed in controlled clinical studies versus placebo a high efficacy in the major depressive disorder. The Applicants has now found that agomelatine, due to its pharmacological properties, can be used in the Generalized Anxiety Disorder.

A clinical study carried out versus placebo on patients suffering from Generalized Anxiety Disorder significantly showed that agomelatine is a really suited treatment for this disorder.

Furthermore, besides the observed efficacy in the treatment of the Generalized Anxiety Disorder, agomelatine has also a good acceptability profile for the patients: particularly, agomelatine is devoid of usually associated side effects of psychotropic drugs. Among those effects, the discontinuation syndrome observed when the treatment is stopped with classical psychotropic drugs, is not observed with agomelatine, which becomes a treatment of choice in this pathology.

The invention accordingly relates to the use of agomelatine, and also its hydrates, crystalline forms and addition salts with a pharmaceutically acceptable acid or base, in obtaining pharmaceutical compositions intended for the treatment of Generalized Anxiety Disorder.

Particularly, the invention relates to the use of agomelatine obtained as crystalline II form described in Patent specification EP 1 564 202, in obtaining pharmaceutical compositions intended for the treatment of Generalized Anxiety Disorder.

The pharmaceutical compositions will be presented in forms suitable for administration by the oral, parenteral, transcutaneous, nasal, rectal or perlingual route, and especially in the form of injectable preparations, tablets, sublingual tablets, glossettes, gelatin capsules, capsules, lozenges, suppositories, creams, ointments, dermal gels etc.

Besides agomelatine and the mood stabiliser optionally associated therewith, the pharmaceutical compositions according to the invention comprise one or more excipients or carriers selected from diluents, lubricants, binders, disintegration agents, absorbents, colourants, sweeteners etc.

By way of non-limiting example there may be mentioned:
  as diluents: lactose, dextrose, sucrose, mannitol, sorbitol, cellulose, glycerol,
  as lubricants: silica, talc, stearic acid and its magnesium and calcium salts, polyethylene glycol,
  as binders: aluminium and magnesium silicate, starch, gelatin, tragacanth, methylcellulose, sodium carboxymethylcellulose and polyvinylpyrrolidone,
  as disintegrants: agar, alginic acid and its sodium salt, effervescent mixtures.

The useful dosage varies according to the sex, age and weight of the patient, the administration route, the nature of the disorder and any associated treatments and ranges from 1 mg to 50 mg of agomelatine per 24 hours.

The daily dose of agomelatine will preferably be 25 mg per day, with a possibility to increase to 50 mg per day.

Pharmaceutical Composition:

Formula for the preparation of 1000 tablets each containing 25 mg of active ingredient:

| | |
|---|---:|
| N-[2-(7-methoxy-1-naphthyl)ethyl]acetamide | 25 g |
| Lactose monohydrate | 62 g |
| Magnesium stearate | 1.3 g |
| Povidone | 9 g |
| Anhydrous colloidal silica | 0.3 g |
| Cellulose sodium glycolate | 30 g |
| Stearic acid | 2.6 g |

Clinical Study:

A clinical study versus placebo has been carried out in 121 patients. Those 121 patients have been randomised in two parallel groups and received either agomelatine at 25 mg per day or placebo.

After treatment for two weeks, and in case of low response, doses have been increased to 50 mg per day in double blind study for patients receiving agomelatine with a IVRS system (Interactive Voice Response System). Treatment for 12 weeks was carried out.

The efficacy has been appreciated with evaluation tools recommended by the health authorities, such as the Hamilton Anxiety Scale (Hamilton M., J. Neurol. Neurosurg. Psychiat., 1959, 23, 56-62), or the Sheehan Disability Scale (International Clinical Psychopharmacology, 1996, 11, 89-95). The acceptability profile has also been evaluated.

The results obtained showed on the total score of the Hamilton scale, first criteria for evaluation, a difference between the group under treatment with agomelatine and the group under placebo of −3.28 (p=0.040), corresponding to a clinically and statistically significant difference.

The study also showed a good acceptability profile for the patients, and the absence of the discontinuation syndrome when the treatment was stopped.

We claim:

1. A method for treating a living animal body afflicted with Generalized Anxiety Disorder comprising the step of monotherapeutically administering to the living animal body an amount of agomelatine, a crystalline form or addition salt thereof with a pharmaceutically acceptable acid or base, which is effective for alleviation of Generalized Anxiety Disorder.

2. The method of claim 1, wherein agomelatine is a crystalline II form.

3. The method of claim 1, wherein the agomelatine is administered in combination with one or more pharmaceutically acceptable excipients.

4. The method of claim 3, wherein agomelatine is a crystalline II form.

5. The method of claim 1, wherein the living animal body is a human.

* * * * *